(12) United States Patent
Adkins, Jr. et al.

(10) Patent No.: US 8,895,080 B2
(45) Date of Patent: Nov. 25, 2014

(54) COMPOSITIONS AND KITS FOR OCULAR TREATMENT

(75) Inventors: Nat Adkins, Jr., Richmond, TX (US); Cynthia Barratt, Richmond, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 100 days.

(21) Appl. No.: 13/350,197

(22) Filed: Jan. 13, 2012

(65) Prior Publication Data

US 2012/0121694 A1 May 17, 2012

Related U.S. Application Data

(63) Continuation-in-part of application No. 12/487,552, filed on Jun. 18, 2009, now abandoned.

(60) Provisional application No. 61/132,583, filed on Jun. 20, 2008.

(51) Int. Cl.
*A61K 36/00* (2006.01)

(52) U.S. Cl.
USPC ............................................. 424/725

(58) Field of Classification Search
USPC ............................................. 424/725
See application file for complete search history.

(56) References Cited

U.S. PATENT DOCUMENTS

| | | | |
|---|---|---|---|
| 3,824,218 A | 7/1974 | McKenna | |
| 4,026,825 A | 5/1977 | Steen et al. | |
| 5,626,856 A | 5/1997 | Berndt | |
| 5,888,493 A | 3/1999 | Sawaya | |
| 6,423,323 B2 | 7/2002 | Neubourg | |
| 2003/0065027 A1* | 4/2003 | Brock et al. | 514/547 |
| 2003/0215530 A1* | 11/2003 | Uehara et al. | 424/729 |
| 2004/0170670 A1* | 9/2004 | Smith et al. | 424/443 |
| 2005/0048020 A1 | 3/2005 | Wille | |
| 2006/0002964 A9* | 1/2006 | Schreiber et al. | 424/401 |
| 2006/0099273 A1* | 5/2006 | Lotan | 424/529 |
| 2009/0061025 A1 | 3/2009 | Gao et al. | |
| 2009/0214676 A1 | 8/2009 | Gao et al. | |
| 2009/0238858 A1* | 9/2009 | Kohn et al. | 424/429 |
| 2009/0317503 A1* | 12/2009 | Adkins et al. | 424/776 |
| 2010/0273870 A1 | 10/2010 | Gao et al. | |

FOREIGN PATENT DOCUMENTS

| | | | |
|---|---|---|---|
| EP | 1685824 A1 | * | 8/2006 |
| KR | 738598 B1 | * | 7/2007 |
| WO | WO 2006/119174 A1 | * | 11/2006 |

OTHER PUBLICATIONS

Helmer Cook and Beautify With Coconut Oil; Better Nutrition; Mar. 2007; 69, 3; ProQuest Central p. 40.*
Wikipedia: Blepharitis; Online Encyclopedia, URL< http://en.wikipedia.org/wiki/Blepharitis> accessed Aug. 20, 2013, archived to Oct. 10, 2007, 5 pages.*
Wikipedia: Medium-Chain Triglyceride; Online, URLhttp://en.wikipedia.org/wiki/Medium-chain_triglyceride accessed Aug. 20, 2013, 3 pages.*
James (Dec. 2007) The Truth About Beauty; Simon & Schuster, Inc., New York, NY, Dec. 2007, p. 329.*
European Commission Health & Consumer Protection Directorate-General, Scientific Committee on Consumer Products, SCCP/0843/04, Opinion on Tea Tree Oil, pp. 1-21, Dec. 7, 2004.
In vitro and in vivo killing of ocular Demodex by tea tree oil, Gao et al., Br J Ophthalmol 2005;89:1468-1473. doi: 10.1136/bjo.2005.072363, p. 1-6.
High Prevalence of Demodex in Eyelashes with Cylindrical Dandruff, Gao et al. Investigate Ophthalmolgy and Visual Science, 46(9), p. 1-12, Sep. 2005.
USPTO Office Action dated Aug. 2, 2011 for parent application U.S. Appl. No. 12/487,552.

* cited by examiner

*Primary Examiner* — Patricia Leith
(74) *Attorney, Agent, or Firm* — D'Ambrosio & Menon, PLLC; Usha Menon

(57) ABSTRACT

Embodiments of the invention provide eyelid preparations, methods, and kits, for treating ocular conditions. The eyelid preparations comprise a mixture of tea tree oil and sea buckthorn oil in a pharmaceutically acceptable carrier.

1 Claim, No Drawings

COMPOSITIONS AND KITS FOR OCULAR TREATMENT

PRIORITY

This application is a continuation in part of U.S. patent application Ser. No. 12/487,552 (now published as U.S. Publication No. 2009/0317503 A1), filed Jun. 18, 2009 which claimed priority to U.S. Provisional Patent Application Ser. No. 61/132,583 filed Jun. 20, 2008.

BACKGROUND

The eyelids are important to ocular health because they protect the eyes from airborne contaminants, such as pollen, dust particles or other foreign bodies. The eyelids contain several glands including the lacrimal glands and the specialized form of the sebaceous glands, the meibomian glands, which produce layers of tear film that are critical for healthy eyes.

The eyelids are subject to problems like blepharitis, dry eyes and inflammation of the meibomian glands. Another complication is the infestation of the arachnid, *Demodex folliculorum* (*Demodex* mites). The *Demodex* mite infestation is common in humans; anecdotal evidence suggests that the mites can be found in ten percent of the eyelashes of healthy persons. The occurrence of the infestation may also be age related.

*Demodex* mites reside inside the sebaceous glands and hair follicles. They cause damage to the cell walls by sucking nutrients from the hair roots. They burrow into the skin, lay eggs, introduce bacteria, and infect the skin. Some of the symptoms of infestation include itching and inflammation of the eyelids. Additionally, there is evidence that the mites can also be one of the causes of the skin disease rosacea.

SUMMARY

Preparations or compositions, methods and kits for the treatment of ocular disorders have been disclosed herein. The one or more embodiments of the invention may be applied to human eyelids or eyelashes. The eyelid preparation may comprise a mixture of tea tree oil, sea buckthorn oil and a medium chain triglyceride. The medium chain triglyceride may comprise caprylic capric triglyceride or any other suitable dermatological carrier for the tea tree oil and sea buckthorn oil.

In another embodiment, a method for treating ocular conditions comprises applying an eyelid preparation comprising tea tree oil, sea buckthorn oil and caprylic capric triglyceride onto a treatment site and allowing the eyelid preparation to penetrate into the treatment site. The eyelid preparation may be rinsed off after a pre-determined duration and re-applied as necessary.

In another embodiment, one or more kits comprising an eyelid preparation comprising tea tree oil, sea buckthorn oil and caprylic capric triglyceride have been disclosed.

The foregoing and other objects, features and advantages of the disclosure will be apparent from the following detailed description of the invention.

DETAILED DESCRIPTION OF THE INVENTION

Mites of the genus *Demodex* are commonly found infesting the area around hair follicles and sebaceous glands in mammals. Two species known to infest humans, include *Demodex folliculorum*, found on the hair follicles of humans and, *Demodex brevis*, infesting the sebaceous glands associated with the hair follicles. Together, these mites are commonly referred to as "eyelash mites". The *Demodex* mites are quite small, adults being in the 0.3 mm to 0.4 mm range. Infestations of the mites on the eyelashes and eyelids are commonly observed. Infestation by *Demodex* mites is common especially in older adult humans.

An overpopulation of the mites may cause a condition known as demodicosis, which leads to inflammation of the skin, itching, and associated skin disorders. An inflammation of the eyelids known as blepharitis can also be caused by *Demodex* infestation. Often associated with or secondary to blepharitis is a bacterial infection of the surface of the skin at the edge of the lid, known as an internal hordeolum. Other such infections include external hordeolum, commonly referred to styes, which are infections of the tiny oil secreting meibomian glands along the edge of the eyelid, surrounding the eyelashes. A stye begins as a red, tender bump and usually fully develops within three days. Such conditions are accompanied by pain, redness and tenderness of the lid margins.

Embodiments of the invention relate to an eyelid preparation that may be effective as a parasiticide to treat or kill *Demodex* mites. In other embodiments, the eyelid preparation can treat or prevent ocular conditions such as dry eyes, blepharitis and meibomianitis or dysfunctions of the meibomian glands that may result from infestations of *Demodex* mites, including *Demodex folliculorum*. The eyelid preparation is designed for application on human or animal skin and hair; particularly the hair and skin of the face, eyelids, and the area around the eyelids of humans. The eyelid preparation may be constituted to take the form of a gel, ointment, cream, lotion or paste. However, the eyelid preparation may be any ocular composition that treats or prevents blepharitis, dry eyes, meibomianitis, and infestations of mite organisms, including *Demodex folliculorum*.

In one or more embodiments, the eyelid preparation may comprise a mixture of tea tree oil and sea buckthorn oil, both of which are essential oils. Essential oils are naturally occurring, hydrophobic liquids extracted from plants. Tea tree oil or melaleuca oil is an essential oil obtained by steam distilling the leaves of the *Melaleuca alternifolia* which is native to the northeast coast of New South Wales, Australia. Tea tree oil contains constituents called terpenoids, a naturally occurring organic chemical. Sea-buckthorn identifies a group of species in the genus *Hippophae rhamnoides*. Sea buckthorn oil can be extracted from either the seeds or the pulp of the fruit. The natural antioxidants and essential fatty acids in the sea buckthorn oil may help reverse damaging effects of sun radiation and minimize long term effects of sun exposure, like wrinkles, dryness, dark spots reduce skin inflammation, promote natural skin restorative processes.

The preparation may further comprise a medium chain triglyceride. For example, in one or more embodiments, the medium chain triglyceride may be caprylic capric triglyceride. Caprylic capric triglyceride slows the loss of water from the skin by forming a barrier on the skin's surface. It is also used to alter the thickness of liquid products. Caprylic capric triglyceride is an oily mixed ester composed of caprylic and capric fatty acids derived from coconut oil and glycerin. The desirability of caprylic capric triglyceride in cosmetics and personal care products is based on its stability, solubility, and lack of odor and color. Due to its low viscosity and excellent oxidative stability, caprylic capric triglyceride is an efficient solvent and therefore acts as a carrier for fat-soluble vitamins and actives.

The preparations may further comprise a preservative. A preservative is an agent that prolongs the useful life of a material. The preservative may additionally possess biocidal properties. A biocide is a substance that kills or inhibits the growth of microorganisms such as bacteria, molds, slimes, fungi, etc. In one or more embodiments, the preservative may comprise sodium perborate or benzylkonium chloride.

In one or more embodiments, the viscosity of the eyelid preparation may be adjusted so that the composition is rapidly absorbed by the eyelids and so that the essential oil does not drip or run into the eyes. In other embodiments of the invention, the gel viscosity may have a range of about 75,000 centipoise to about 3,000,000 centipoise to aid the absorption of the eyelid preparation.

In one or more embodiments, the eyelid preparation may comprise 45% to 55% tea tree oil, and 15% to 25% sea buckthorn oil. The eyelid preparation may further comprise 25% to 35% caprylic capric triglyceride.

In one or more embodiments, the eyelid preparation may comprise 50% tea tree oil, 20% sea buckthorn oil, and 30% caprylic capric triglyceride. The combination of tea tree oil and sea buckthorn oil in this particular ratio has been found to be extremely beneficial in the treatment of *Demodex* mites.

Test Results

Patient was an 80 year old man who had severe *Demodex* infestation on his eyelashes. A test of the eyelashes revealed that it was teeming with more than twelve mites. The patient was treated with a composition comprising 50% tea tree oil, 30% caprylic capric triglyceride and 20% sea buckhorn oil. A month later the eyelashes were re-examined. It was found to have no mites and the *Demodex* infestation appeared to be completely cured.

One or more embodiments of the invention relate to methods for treating ocular conditions. The methods may involve the identification of a treatment site and the application of an eyelid preparation thereto. The treatment site may be the eyes or the skin or hair follicles surrounding the eyelids. An applicator may be coated with the eyelid preparation (in accordance with any of the eyelid preparation compositions described above) for application to and penetration into the treatment site. For example, in one or more embodiments, the eyelid preparation to be used may comprise 45% to 55% tea tree oil, 15% to 25% sea buckthorn oil, and 25% to 35% caprylic capric triglyceride. The methods may further involve allowing the eyelid preparation to penetrate into the treatment site.

Single-use or multi-use applicators may be impregnated with or coated with the eyelid preparation. Various types of applicators may therefore be used, including, but not limited to, brushes, cotton swabs, and polymer meshes. Once treatment is completed, the applicator may be discarded and the treated area rinsed to remove any excess chemicals.

In one embodiment, the applicator comprises a fabric pad. A person skilled in the art will recognize that numerous fabric and fabric blends may be chosen for the applicator. The fabric may be natural, synthetic, or a blended weave. The ideal fabric is gentle enough to be used on the eyelids and the sensitive skin surrounding the eyes, but is also rough enough or textured enough to provide a significantly tactile surface to effectively treat the eyelids. Furthermore, the fabric pad must have sufficient loft and interstitial spaces to hold the eyelid preparation in the fabric weave long enough to effectively apply the eyelid preparation to the treatment site.

The fabric pads may be of a disposable or reusable nature. In one embodiment, fabric pads are pre-moistened and/or pre-coated with the eyelid preparation and are placed in a sealed pouch or sealable container to protect the contents of the pouch from the environment. The sealable container may further comprise a box, or a package. The package may be made of any suitable material including plastic or a metal foil material. The pre-coated fabric pads may be individually packaged for use.

The applicator may be disposable, as discussed herein. Alternately, the thumb or other fingers may be used to apply the eyelid preparation of the invention. The eyelid preparation is dispensed to the treatment site with the applicator. The eyelid preparation is designed to stay on the treatment site long enough for the active ingredients, the essential oils, to penetrate and to be properly absorbed, but without lingering too long on the skin prior to absorption, thus causing a feeling or "greasiness", uneasiness, or discomfort to patient. In one embodiment, the eyelid preparation has a viscosity that allows rapid absorption into the treatment site while avoiding leakage of the eyelid preparation into the eye.

In another embodiment, a method for applying an eyelid preparation on human eyelids or eyelashes infected with *Demodex* mites comprises coating an applicator with the eyelid preparation. The applicator is manipulated for application of the eyelid preparation on the eyelids or the eyelashes. The eyelid preparation is allowed to remain on the eyelids or the eyelashes for a pre-determined time period. The applicator is discarded after the application of the eyelid preparation is completed.

The eyelid preparation may be readily removable and washable without the use of harsh or damaging cleansers. In one embodiment, the eyelids or the eyelashes may be rinsed with saline after the pre-determined time period. The pre-determined time period may range from 5 minutes to 10 minutes. In other aspects, the eyelid preparation may be reapplied after a rest period. The rest period may range from 5 minutes to 20 minutes. Following the rest period, the eyelid preparation may be reapplied for another 5-10 minute period. This treatment is repeated weekly until the *Demodex* infestation is completely destroyed.

One or more embodiments of the invention relate to kits for treating ocular conditions. Such ocular conditions may comprise one or more conditions selected from a group consisting of: meibomian gland dysfunctions, blepharitis, dry eyes, and infestations of *Demodex* mites.

In one or more embodiments, the kit may comprise an eyelid preparation, and instructions to dispense a pharmaceutically effective amount of the eyelid preparation to a subject in need of treatment. The eyelid preparation may comprise any of the eyelid preparation compositions described above. For example, in one or more embodiments, the eyelid preparation may comprise 50% tea tree oil, 20% sea buckthorn oil, and 30% caprylic capric triglyceride.

In one or more embodiments, the kit may comprise an eyelid preparation, and an eyelid scrub. The eyelid preparation may comprise 45% to 55% tea tree oil, 15% to 25% sea buckthorn oil, and 25% to 35% caprylic capric triglyceride.

In one or more embodiments, the eyelid scrub may comprise eyelid scrub-related matter disclosed in U.S. Pat. No. 7,951,387, which is incorporated herein by reference in its entirety. Where a definition or use of a term in the incorporated reference is inconsistent or contrary to the definition of that term provided herein, the definition of that term provided herein applies and the definition of that term in the reference does not apply. In one or more embodiments, for example, the eyelid scrub included in the kit may be one or more eyelid scrubs sold as OCuSOFT® Lid Scrub®.

In one or more embodiments, the kit may comprise an eyelid preparation, and a liposome spray. The eyelid preparation may comprise 45% to 55% tea tree oil, 15% to 25% sea buckthorn oil, and 25% to 35% caprylic capric triglyceride.

The liposome spray may be a cooling mist that provides relief from eyelid irritation. The liposome spray may be used in conjunction with an eyelid scrub to provide soothing relief throughout the day. Computer Vision Syndrome (CVS) is a growing condition that demands lubrication to help prevent moisture loss. A liposome spray such as TEARS AGAIN® Advanced Liposome Spray, for example, may be used to refresh and protect against moisture loss.

Liposomes are microscopic molecules that have been used for years in cosmetic and drug delivery. Vital nutrients and antioxidants that include Vitamins A, C, and E have been added to provide relief from eyelid irritation. These antioxidants may also reduce the appearance of fine lines and wrinkles around the eyes and eyelids.

In one or more embodiments, the kit may comprise an eyelid preparation, and one or more pre-moistened pads. The eyelid preparation may comprise 45% to 55% tea tree oil, 15% to 25% sea buckthorn oil, and 25% to 35% caprylic capric triglyceride. The pre-moistened pads may be used to remove oil, debris and desquamated skin from the eyelids.

In one or more embodiments, the kit may comprise an eyelid preparation, a liposome spray, and one or more pre-moistened pads. The eyelid preparation may comprise 45% to 55% tea tree oil, 15% to 25% sea buckthorn oil, and 25% to 35% caprylic capric triglyceride. The pre-moistened pads may be used to remove oil, debris and desquamated skin from the eyelids.

In one or more embodiments, the kit may comprise: an eyelid preparation; a blephbrush; a liposome spray; a lubricating ointment for the eye; and one or more fabric pads for removing oil, debris and desquamated skin from the eyelids. The eyelid preparation may comprise 50% tea tree oil, 20% sea buckthorn oil, and 30% caprylic capric triglyceride. The blephbrush may be a two-sided cosmetic brush used for removing debris from the eyelids and eyelashes. The lubricating ointment may comprise an ointment that may be used to provide relief from dry eye symptoms, and/or used as a lubricant to prevent further irritation to the eye. In one or more embodiments, the lubricating ointment may comprise a mixture of mineral oil and white petrolatum. For example, in one or more embodiments, TEARS AGAIN® Sterile Lubricant Eye Ointment may be included in the kit.

In one or more embodiments, the fabric pads may be pre-coated with an eyelid preparation comprising 45% to 55% tea tree oil, 15% to 25% sea buckthorn oil, and 25% to 35% caprylic capric triglyceride. Further, in one or more embodiments, the fabric pads may be pre-coated with an eyelid scrub solution. In one or more embodiments, the eyelid scrub solution may comprise eyelid scrub solution disclosed in U.S. Pat. No. 7,951,387.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

The invention claimed is:

1. A kit for treating ocular conditions selected from a group consisting of meibomian gland dysfunctions, blepharitis, dry eyes, and infestations of *Demodex* mites, the kit consisting of:
   an eyelid preparation comprising:
      45% to 55% tea tree oil;
      15% to 25% sea buckthorn oil;
      25% to 35% caprylic capric triglyceride; and
      a preservative comprising sodium perborate or benzalkonium chloride
   a brush for removing debris from eyelids and eyelashes;
   a spray comprising a liposome;
   a lubricating ointment comprising mineral oil and petrolatum;
   one or more pre-moistened pads for removing oil, debris and desquamated skin from the eyelids, and
   instructions to dispense a pharmaceutically effective amount of the eyelid preparation to a subject in need of treatment, and
   wherein the eyelid preparation is a gel, ointment, cream, lotion or paste.

* * * * *